United States Patent [19]

Burton et al.

[11] Patent Number: 4,682,583
[45] Date of Patent: Jul. 28, 1987

[54] INFLATABLE ARTIFICIAL SPHINCTER

[76] Inventors: John H. Burton, 13110 Greenwood Rd., Minnetonka, Minn. 55343; Brad G. Staehle, 17220 Creek Ridge Pass, Minnetonka, Minn. 55345

[21] Appl. No.: 600,107

[22] Filed: Apr. 13, 1984

[51] Int. Cl.⁴ .............................................. A61B 17/00
[52] U.S. Cl. .................................... 128/1 R; 128/325; 128/346; 128/DIG. 25
[58] Field of Search .................................. 604/97-99; 128/79 A, 325, 346, DIG. 25, 1 R

[56] References Cited

U.S. PATENT DOCUMENTS

| | | | |
|---|---|---|---|
| 3,744,063 | 7/1973 | McWhorter et al. | 3/1 |
| 3,863,622 | 2/1975 | Buuck | 128/1 R |
| 3,954,102 | 5/1976 | Buuck | 128/79 A |
| 4,222,377 | 9/1980 | Burton | 128/1 R |
| 4,256,094 | 3/1981 | Kapp et al. | 128/325 X |
| 4,412,530 | 11/1983 | Burton | 128/346 |

Primary Examiner—Stephen C. Pellegrino
Attorney, Agent, or Firm—Arnold, White & Durkee

[57] ABSTRACT

A semi-automatic functioning artificial sphincter including a means for occluding a body passage, a fluid reservoir, and a mechanism for transferring fluid between the occluding mechanism and the fluid reservoir, wherein the sphincter also includes a lock-out mechanism for occluding fluid flow between the fluid reservoir and the inflatable cuff and the occluding mechanism. The occluding mechanism is preferably a valve which is positioned in the fluid path between the reservoir and the occluding mechanism. The valve may be either manually or hydraulically actuated to control one or more aspects of fluid flow through the valve.

8 Claims, 7 Drawing Figures

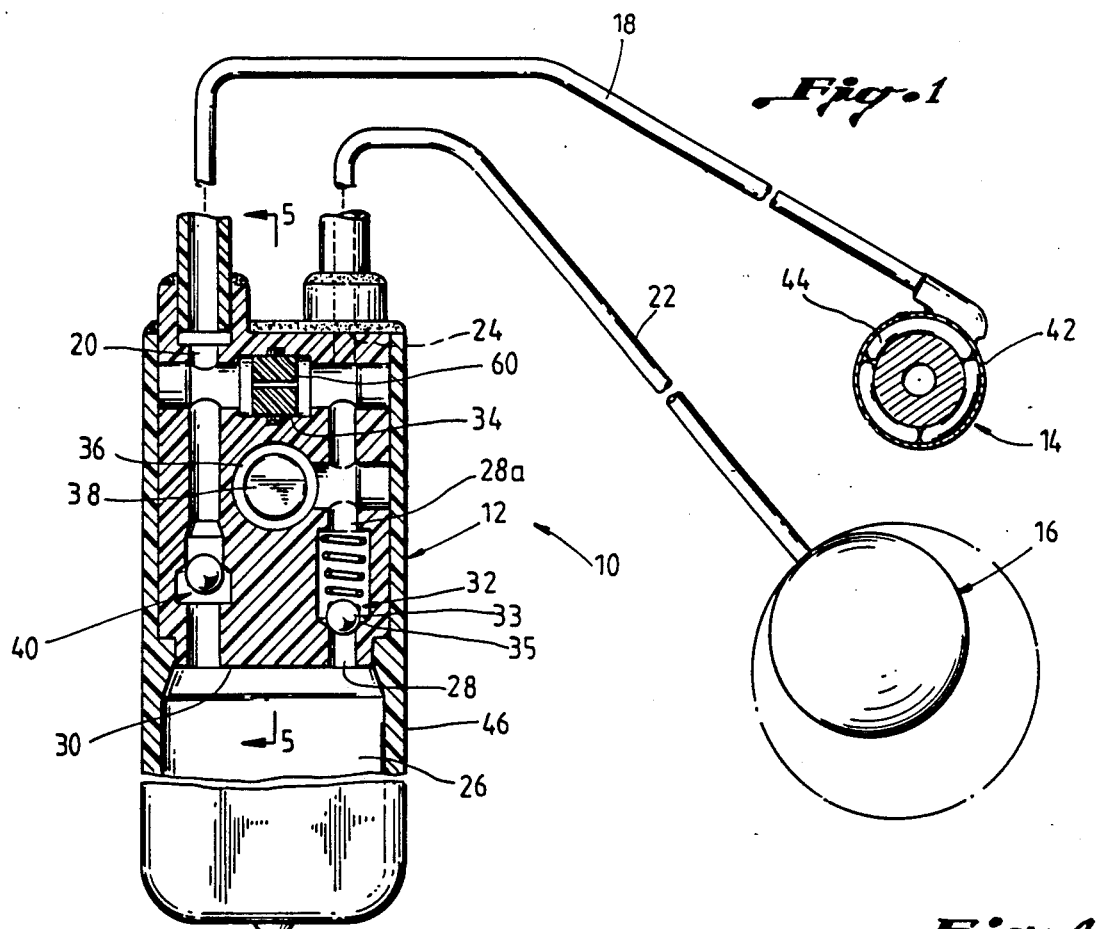

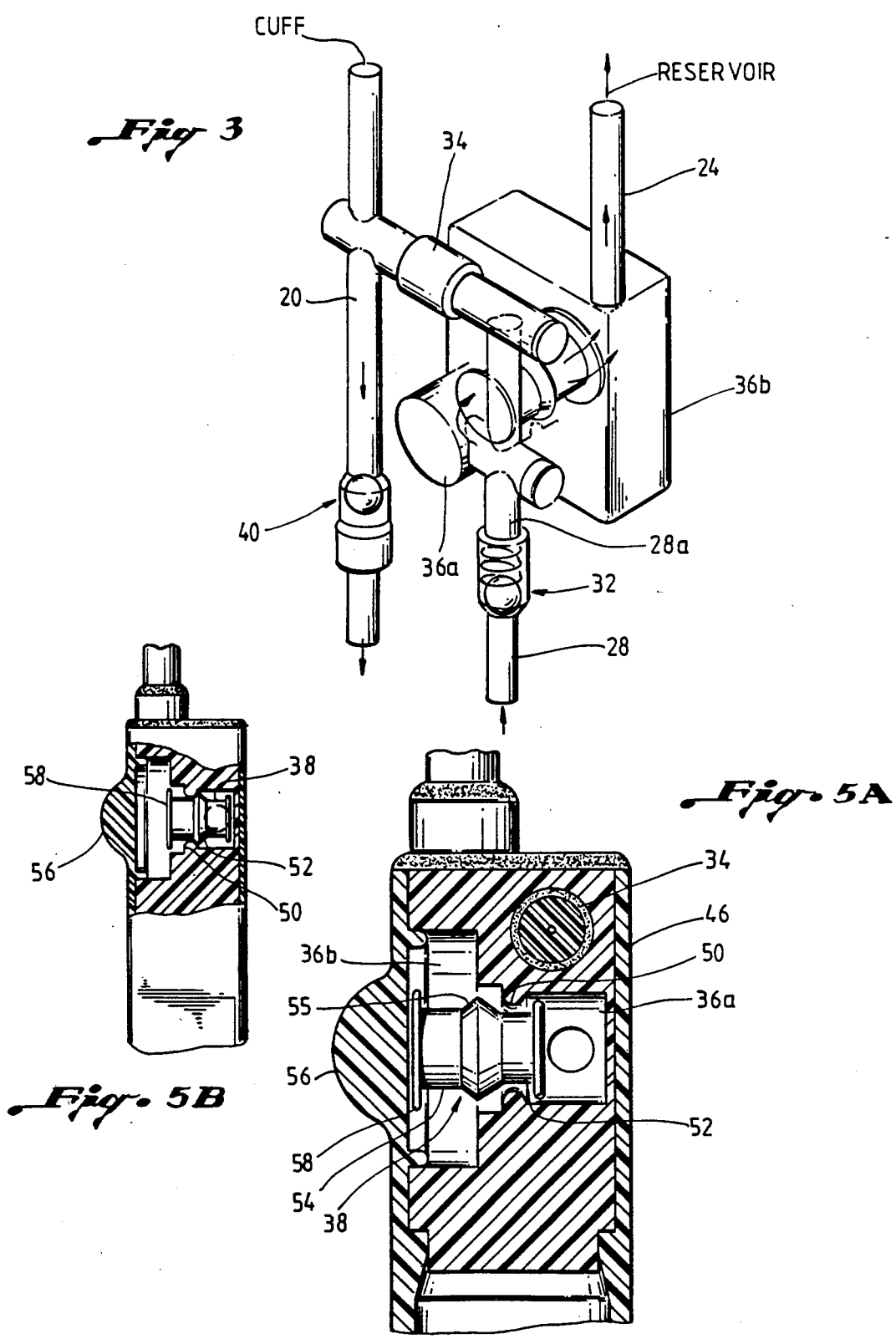

4,682,583

INFLATABLE ARTIFICIAL SPHINCTER

BACKGROUND OF THE INVENTION

This invention relates generally to methods and apparatus for treating incontinence and more specifically relates to methods and apparatus for providing an inflatable artificial sphincter for control of excretory body passages.

A known treatment for some cases of incontinence is to provide an individual with a mechanism to occlude the affected excretory body passage. These mechanisms are typically surgically implanted within the individual and are adapted to be operable by the individual to selectively open and occlude the body passage and to ease coping with the incontinence.

Inflatable artificial sphincters are one known form of such mechanism. Inflatable sphincters typically include an inflatable cuff for surrounding the passage to be occluded. One or more pumps cooperatively associated with a fluid reservoir are utilized to transfer fluid into and out of the cuff. As fluid is pumped into the cuff, the cuff inflates and closes the circumscribed body passage. One difficulty with inflatable sphincters concerns their implantation within the patient. When the cuff of the device is initially placed around the intended body passage, the passage is irritated by the foreign body. If the cuff is inflated during the period in which the passage adapts to the presence of the cuff, the likelihood of erosion and/or scarring occlusion of the passage is significantly increased. It is therefore desirable to maintain the cuff in an uninflated condition while the passage adapts to the presence of the cuff.

One type of inflatable artificial sphincter which offers significant benefits to the patient is a semi-automatic functioning sphincter wherein the pump transfers fluid from the cuff to a fluid reservoir to open the body passage. The fluid then gradually returns to the cuff over a limited period of time to refill the cuff and occlude the body passage. This refilling occurs without the necessity of any additional manipulation by the individual. Thus, the manipulation of a single pump facilitates the desired continence to the individual. Because prior art types of these sphincters allow the cuff to reinflate automatically, various techniques have had to be adapted to protect the body passage during the adaption period.

Previously utilized techniques for maintaining the cuff in an uninflated condition during the initial adjustment period have included implanting the inflatable sphincter without the fluid used to inflate the cuff. After the period of adaptation has passed, the sphincter is filled with fluid and allowed to function normally. Another technique for maintaining the cuff in an uninflated condition which has been utilized is to implant an auxiliary occluding mechanism around the tubing connecting the sphincter reservoir to the pump. This auxilary occluding mechanism is added solely for occluding the artificial sphincter tubing and does not form a part of the artificial sphincter itself. This mechanism is utilized to occlude the tubing and to thereby lock the fluid into the reservoir. The auxiliary occluding mechanism is then later released to allow normal operation of the sphincter. Both of these techniques require an additional surgical procedure to place the sphincter in normally operating condition. This is inefficient and inconvenient for both patient and physician.

Accordingly, the present invention provides a new method and apparatus whereby fluid may be selectively locked out of the cuff of an inflatable sphincter by an externally operable mechanism, and whereby such mechanism is repeatedly operable to perform such lockout function or to allow normal operation of the sphincter.

SUMMARY OF THE INVENTION

The present invention includes a means for occluding the fluid flow between the fluid reservoir and the inflatable cuff in an automatically refilling inflatable artificial sphincter as described above. In a preferred embodiment, the invention includes a valve positioned to selectively occlude passage of fluid into or out of the fluid reservoir. In a particularly preferred embodiment, the valve is manually actuable to close the fluid flow, but is hydraulically actuable to open the fluid flow. This design facilitates operation of the valve and thereby convenience to the individual.

BRIEF DESCRIPTION OF THE DRAWINGS

FIG. 1 illustrates an artificial sphincter in accordance with the present invention, with the pump and valving unit of the sphincter illustrated partially in vertical section.

FIG. 2 is a schematic illustration of the artificial sphincter of FIG. 1.

FIG. 3 is a perspective illustration of the fluid flow areas of the pump and valving unit shown in FIG. 1.

FIG. 4 is a side view of the pump and valving mechanism of the artificial sphincter illustrated in FIG. 1.

FIGS. 5A-B are side views of the poppet valve portion of the pump and valving unit shown in FIG. 1, illustrating the poppet valve in first and second positions, respectively.

DETAIL DESCRIPTION OF A PREFERRED EMBODIMENT

Referring now to the drawings in more detail, and particularly to FIGS. 1 and 2, therein is shown in FIG. 1 an inflatable artificial sphincter in accordance with the present invention, and in FIG. 2 a schematic illustration of the artificial sphincter of FIG. 1. Artificial sphincter 10 includes a pump and valving unit ("pump") 12, inflatable cuff 14 and balloon or reservoir 16. A first tube 18 provides fluid communication between cuff 14 and a first passage 20 in pump 12. A second tube 22 provides fluid communication between reservoir 16 and a second passage 24 in pump 12.

Pump 12 includes a pump bulb portion 26 in fluid communication with passages 20 and 28. Passageway 28 includes a check valve 32. Check valve 32 is preferably spring-biased and most preferably is of the ball and seat type wherein the ball is spring-biased toward the seat. Check valve 32 is oriented to allow the flow of fluid away from pump bulb 26 but not into pump bulb 26.

The portion of passageway 28 downstream of check valve 32, designated for clarity 28a, communicates both with fluid resistance element 34 and poppet valve chamber 36a. Fluid resistance element 34 provides a generally predetermined resistance to fluid flow between passages 28a and 20b. Fluid resistance element 34 may be of several types known to the art, but preferably is a resistance element defining a labyrinth-type fluid passage such as one formed by a plurality of axially-aligned, perforated disks adapted to define a restrictive path to fluid flow. Poppet valve chamber 36 includes poppet 38 which selectively blocks fluid flow between poppet valve chamber portions 36a and 36b. Poppet 38 and poppet valve chamber 36 will be discussed in more detail in reference to FIG. 5.

Passageway 20 includes a check valve 40. Check valve 40 is preferably of the ball and seat type and preferably is not spring-biased. Check valve 40 is oriented to allow fluid flow only into pump chamber 26.

In one preferred embodiment, reservoir 16 is a single elastic envelope having a generally predetermined and consistent coefficient of expansion pressure, i.e., when fluid is pumped into reservoir 16, causing it to expand, the elasticity of reservoir 16 will exert a generally constant pressure upon such fluid, relatively independent of the volume of fluid which is pumped into reservoir 16, and the consequential degree of expansion of reservoir 16.

Cuff 14 preferably includes a generally non-elastic backing 42 and an inflatable cushion 44.

Because the entire artificial sphincter 10 is implanted within the patients body, all external surfaces of artificial sphincter 10 are formed of a physiologically inert material. In particular, external sheath 46 of pump 12 is preferably formed of silicon rubber. This silicon rubber construction of external sheath 46 allows optimal flexibility of external sheath 46 to facilitate operation of pump bulb 26. Additionally, pump body 30 of pump 12, in which the described passages and chambers are situated, is also preferably formed of silicon rubber. If pump body 30 is formed of another, less resilient material, it is desirable that the seats of check valves 32 and 40 be formed of a resilient material, such as silicon rubber, to assure optimal operation of the valves.

Referring now to FIG. 3 of the drawings, therein are shown the fluid flow paths in pump 12 of FIG. 1, illustrated in perspective view. Arrows are shown depicting the fluid flow paths which exist at the time pump bulb 26 is operated to effect deflation of cuff 14. The operation of artificial sphincter 10 and the fluid flow will be discussed in greater detail in the discussion of the operation of the device.

Referring now to FIGS. 4 and 5A-B, therein is shown in FIG. 4 pump bulb 12, illustrated in side view, and in FIG. 5, therein is shown the upper portion of pump 12 containing poppet chamber 36, depicted in reverse side view relative to FIG. 4, and in vertical section. As discussed earlier herein, poppet chamber 36 includes two portions 36a and 36b. Poppet 38 is cooperatively conformed with the boundaries of poppet chamber 36 such that poppet 38 may be retained in either of two positions, the first of these positions, as illustrated in FIG. 5A, allowing the transfer of fluid between poppet chamber 36a and 36b, and a second position, illustrated in FIG. 5B, which prevents such fluid communication between poppet chambers 36a and 36b. In the preferred embodiment illustrated in FIGS. 5A-B, this cooperative conformity between the defining perimeter of poppet chamber 36 and poppet 38 includes a ledge 50 projecting radially inwardly to define a radius within poppet chamber 36. At least this ledge portion 50 of pump body 30 is generally flexible. Poppet 38 includes a first portion 52 with a diameter which is sufficiently smaller than the radius defined by ledge 50 to allow fluid flow between the surfaces of poppet 38 and ledge 50 when poppet 38 is in the first position, as illustrated in FIG. 5A. Poppet 38 includes a second portion 54 which is of a second, greater, diameter and which is appropriately sized to lie in sealing engagement with ledge 50 when poppet 38 is in the second position, wherein second portion 54 is proximate ledge 50. Longitudinally between first portion 52 and second portion 54 on poppet 38 is a circumferential radially extending surface 55 appropriately sized to be movable past ledge 50 but to provide a reliable detent for poppet 38 when poppet 38 is moved from either position to the other. The size of ledge 50 relative to poppet surface 55, as well as the flexibility of ledge 50, will define the detent force required to move poppet 38 from the second position to the first position. This detent force is preferably a force which can be hydraulically achieved by actuation of pump bulb 36 as limited by the fluid transfer capability of fluid resistance element 34, i.e., the detent force of poppet 38 should be one which is achievable by actuation of pump 26 without the fluid "bleeding off" through fluid resistance element 34 without moving poppet 38 from the second position to the first position. Poppet 38 preferably includes a top 58 which extends radially relative to second portion 54 to insure that poppet 38 remains in the proper orientation relative to ledge 50.

In the preferred embodiment illustrated in FIG. 5, external sheath 46 of pump 12 includes an externally extending node 56 proximate top 58 of poppet 38. Node 56 serves to locate the position of poppet 38 to facilitate actuation by the patient or physician. In the preferred embodiment depicted in FIG. 5, top 58 of poppet 38 lies proximate, but is not coupled to external sheath 46 of pump 12. Alternatively, poppet 38 may be coupled, such as by an adhesive, to external sheath 46. Those skilled in the art will recognize that poppet 38, external sheath 46 and node 56 may be of other conformities. For example, node 56 may be generally hollow and poppet 38 may conformed to fit within the hollow of the node. Additionally, node 56 may be omitted such that external sheath 46 is flat proximate poppet 38.

Those skilled in the art will recognize that other types of positive lock-out valves may be utilized in accordance with the present invention. For example, a valve which is not releasable by hydraulic pressure, but which requires manual manipulation to both open and close the fluid path may be utilized. Because manual manipulation of such a valve in a reciprocating motion would require the use of two hands, one to grasp the pump and hold it stationary relative to the valve poppet, and the other to move the poppet, it is desirable to utilize a valve arrangement wherein pressure in one direction will cause a blocking of the fluid flow and whereby pressure in another, preferably perpendicular direction will open the fluid flow, thereby facilitating operation of the valve with only one hand.

Referring now to FIGS. 1-5 generally, in the normal operation of artificial sphincter 10, when it is desired to deflate cuff 14, pump bulb 26 will be actuated by pressing inwardly on the sides of external sheath 46 in the area defining pump bulb 26. Fluid within pump bulb 26 will be urged toward check valve 32, urging ball 33 off seat 35, and will pass through conduit 28a to be in communication with both poppet chamber 36a and first side 60 of fluid resistance element 34. Assuming that poppet 38 is in the first position (as illustrated in FIG. 5A) the fluid will most readily flow to poppet chamber 36a and from there to poppet chamber 36b, through passage 24 to tube 22 and into reservoir 16. During the actuation of pump bulb 26, as external sheath 46 is released, allowing pump bulb 26 to return to its original dimension, fluid will be drawn from inflatable cushion 44 in cuff 14, through tube 18 into passage 20, through check valve 40 and passage 20 and into pump bulb 26. This type of fluid transfer will occur so long as pump bulb 26 is actuated until inflatable cushion 44 is essentially deflated. At such time, the artificial occlusion of passage 13 is eliminated and normal excretory functions may occur.

As fluid is transferred into reservoir 16, reservoir 16 expands to exert a generally constant pressure on fluid contained therein. When the actuation of pump bulb 26 ceases, the fluid pressure established by reservoir 16 will urge the fluid contained therein to pass back through tube 22 and into pump 12. This fluid may not return to pump chamber 26 due to the operation of check valve 32. Therefore, the fluid will be urged through fluid resistance element 34 at a generally predetermined rate. This rate will allow an essentially known period of time for excretory functions to occur before the contracting force of the reservoir causes fluid to refill both inflatable cushion 44 in cuff 14 and pump chamber 26 (by way of passage 20 and check valve 40). The reinflating of inflatable cushion 44 again establishes occlusion of passage 13 with the pressure of such occlusion maintained at a generally established level by reservoir 16.

If, however, it is desired to maintain the cuff in an uninflated condition, for reasons such as allowing a normal healing time after implantation of artificial sphincter 10 as described earlier herein, poppet valve 38 may be manually actuated and moved to the second position, as illustrated in FIG. 5B. In this second position, poppet 38 blocks fluid transfer between poppet chambers 36a and 36b, thereby preventing fluid from passing from reservoir 16 and poppet chamber 36b in fluid communication therewith, back to cuff 14 by way of fluid resistance element 34. When normal operation of artificial sphincter 10 is desired, squeezing of pump bulb 26 will generate sufficient fluid pressure to move poppet 38 to its first position (as illustrated in FIG. 5A) and allow the fluid transfer discussed above. Additionally, if it is desired to secure cuff 14 in an inflated condition, the movement of poppet 38 to the second position will lock fluid into cuff 14 against the pressure exerted upon the cuff by the excretory passage.

Many modifications and variations besides those specifically mentioned herein may be made in the structures and techniques described herein and depicted in the accompanying drawings without departing from the concept of the present invention.

We claim:

1. An artificial sphincter, comprising:

inflatable fluid operated occlusion means for occluding a body passage;

a fluid reservoir;

a flow passage adapted to provide restricted fluid communication between said occlusion means and said reservoir, said passage arranged such that fluid tends to drain from said reservoir into said occlusion means through said passage;

a pump means in fluid communication with said occlusion means for selectively transferring fluid from said occlusion means to said reservoir to deflate said occlusion means so that the body passage may be opened; and locking means, located along said flow passage, for selectively occluding the flow of fluid from said reservoir to said occlusion means through said flow passage.

2. The artificial sphincter of claim 1, wherein said inflatable occlusion means comprises a cuff adapted to surround said body passage.

3. The artificial sphincter of claim 2, wherein said cuff comprises:

a generally non-stretchable sheath; and at least one inflatable cushion retained proximate said body passage by said sheath.

4. The artificial sphincter of claim 1, wherein said pump comprises:

a flexible member defining a pump bulb;

a first passage allowing fluid communication between said pump bulb and said cuff; and a second passage allowing fluid communication between said pump bulb and said fluid reservoir.

5. The artificial sphincter of claim 1, wherein said fluid reservoir is placed in restricted fluid communication with said inflatable occlusion means by a fluid resistance element.

6. The artificial sphincter of claim 5, wherein said locking means comprises a valve in said second passage, said valve located between said reservoir and said resistance element, said valve allowing selective fluid communication between said reservoir and said fluid resistance element.

7. The artificial sphincter of claim 6, wherein said valve is in fluid communication with said pump and said reservoir.

8. The artificial sphincter of claim 7, wherein said valve is manually operable to occlude the flow of fluid from said reservoir to said occlusion means and manually operable by operating said pump to allow fluid flow from said reservoir to said occlusion means.

* * * * *

UNITED STATES PATENT AND TRADEMARK OFFICE
CERTIFICATE OF CORRECTION

PATENT NO. : 4,682,583
DATED : July 28, 1987
INVENTOR(S) : John H. Burton and Brad G. Staehle It is certified that error appears in the above-identified patent and that said Letters Patent are hereby corrected as shown below:

In the Abstract, first line, "semi-automatic" should read --semi-automatically--.

Signed and Sealed this

Third Day of May, 1988

Attest:

DONALD J. QUIGG

*Attesting Officer*

*Commissioner of Patents and Trademarks*